(12) United States Patent
Borok

(10) Patent No.: US 10,864,189 B2
(45) Date of Patent: Dec. 15, 2020

(54) TOPICAL COMPOSITIONS COMPRISING POLYOLPREPOLYMERS, STEM CELL, AND CANNABINOIDS FOR SKIN CARE

(71) Applicant: Jenna Borok, San Diego, CA (US)

(72) Inventor: Jenna Borok, San Diego, CA (US)

( * ) Notice: Subject to any disclaimer, the term of this patent is extended or adjusted under 35 U.S.C. 154(b) by 0 days.

(21) Appl. No.: 16/455,002

(22) Filed: Jun. 27, 2019

(65) Prior Publication Data

US 2020/0000765 A1    Jan. 2, 2020

Related U.S. Application Data

(60) Provisional application No. 62/692,178, filed on Jun. 29, 2018.

(51) Int. Cl.
| | | |
|---|---|---|
| *A61K 36/00* | (2006.01) | |
| *A61K 31/352* | (2006.01) | |
| *A61K 8/49* | (2006.01) | |
| *A61K 8/34* | (2006.01) | |
| *A61K 8/38* | (2006.01) | |
| *A61K 31/05* | (2006.01) | |
| *A61K 36/185* | (2006.01) | |
| *A61P 17/00* | (2006.01) | |
| *A61K 8/92* | (2006.01) | |
| *A61K 9/00* | (2006.01) | |

(52) U.S. Cl.
CPC ............ *A61K 31/352* (2013.01); *A61K 8/345* (2013.01); *A61K 8/347* (2013.01); *A61K 8/38* (2013.01); *A61K 8/498* (2013.01); *A61K 8/4973* (2013.01); *A61K 8/922* (2013.01); *A61K 9/0014* (2013.01); *A61K 31/05* (2013.01); *A61K 36/185* (2013.01); *A61P 17/00* (2018.01)

(58) Field of Classification Search
CPC ..................................................... A61K 36/00
USPC ........................................................ 424/725
See application file for complete search history.

(56) References Cited

U.S. PATENT DOCUMENTS

2016/0101063 A1*   4/2016   Yeshurun ............. A61K 31/573
                                                              514/729

* cited by examiner

*Primary Examiner* — Michael V Meller
(74) *Attorney, Agent, or Firm* — Procopio, Cory, Hargreaves & Savitch LLP

(57) ABSTRACT

The present invention relates to compositions and methods for the prevention and treatment of skin disorders. In particular, the application describes topical compositions and methods of treatments comprising the combined use of one or more cannabinoids, or use of an ingredient that works on the endocannabinoid system, such as but not limited to, Palmitoylethanolamide (PEA), polyolprepolymers and stem cell extract.

15 Claims, No Drawings

TOPICAL COMPOSITIONS COMPRISING POLYOLPREPOLYMERS, STEM CELL, AND CANNABINOIDS FOR SKIN CARE

RELATED APPLICATION

This application claims the benefit of U.S. provisional application no. 62/692,178, filed Jun. 29, 2018 which is hereby incorporated by reference.

FIELD OF THE INVENTION

The present invention relates to compositions and methods for the prevention and treatment of skin disorders.

BACKGROUND OF THE INVENTION

The skin is the largest organ of the body, with a surface area of 18 square feet. In the epidermis, the keratinocytes produce keratin, a protein that gives skin its strength and flexibility and waterproofs the skin surface. Collagen and elastic fibers in the dermis give strength to the skin. The skin is continuously exposed to changes in the external environment, including oxidative insults, heat, cold, UV radiation, injury, and mechanical stresses. The stratum corneum, composed of terminally differentiated keratinocytes, constitutes the natural barrier that prevents loss of water and penetration of infectious agents, such as bacteria and viruses, and foreign particles. Keratin intermediate filaments provide the cells with mechanical resilience and protects them against physical stress. Disruption of the keratin scaffold leads to tissue and cell fragility in the skin and its appendages (hair, nail, glands), oral mucosa, and cornea, and exposes the skin to pathological conditions and diseases.

Dermatitis, also known as eczema, is an inflammation of the skin that is characterized by the presence of itchy, erythematous, vesicular, weeping, and crusting patches. Inflammatory agents include bacteria, fungi, viruses, and autoimmune, allergic, hormonal and malignant inflammatory agents. The most common skin diseases or disorders include eczema, psoriasis, dermatitis, itching dermatosis, rosacea, perioral dermatitis, acne, non-melanoma skin cancer and melanoma. Although symptoms vary, recurrent dermatitis conditions include pruritus, dryness and skin rashes, which may be accompanied by redness, skin swelling, itching and dryness, crusting, flaking, blistering, cracking, oozing, or bleeding. Common forms of dermatitis include atopic dermatitis and xerotic eczema.

Sunlight is a major cause of skin aging. Symptoms of photoaging are wrinkles, pigmentation, decreased skin elasticity, irregular texture and dryness. While treatment with moisturizers and steroid creams may temporarily control skin disorder and aging symptoms by reducing inflammation and smoothing wrinkles, the relief is only temporary. There is no known cure for dermatitis.

Accordingly, there is a need in the art for improved treatment options for improving skin condition, delaying and reducing the effects of skin aging and treating or preventing skin disorders.

SUMMARY OF THE INVENTION

It is, therefore, an object of the invention to provide solutions to the aforementioned problems, among other objects.

The present invention relates to compositions and methods for the prevention and treatment of skin disorders. In particular, provided herein are topical compositions and methods of treatment, comprising the combined use of one or more cannabinoids, or use of an ingredient that works on the endocannabinoid system, such as but not limited to, Palmitoylethanolamide (PEA), polyolprepolymers and stem cell extract.

In other embodiments, the present invention relates to the use of polyolprepolymers, stem cell medium extract and cannabinoids or compounds that act on endocannabinoid receptors for skin care.

One embodiment of the invention is a topical composition for treating skin that comprises a therapeutically effective amount of at least one cannabinoid or molecule that acts on endocannabinoid receptors (e.g., Palmitoylethanolamide (PEA)), and a therapeutically effective amount of a polyolprepolymer, stem cell extract and BV-OSC (tetrahexyldecy ascorbate). In other embodiments, at least one cannabinoid and either one up to all three of polyolprepolymer, stem cell extract and BV-OSC (tetrahexyldecy ascorbate), may be the only active ingredients of the composition. In one aspect of the linvention, the cannabinoids are present in the topical composition in a concentration between 0.1 and 30% by weight of the composition. Preferably, the cannabinoids are one or more of a natural phytocannabinoid, an organic cannabinoid, an endocannabinoid, a cannabinoid analog, a cannabinoid derivative, a synthetic cannabinoid and a cannabinoid receptor agonist. The polyolprepolymers include all compositions for facilitation permeation enhancement of the product into the skin outlined in U.S. Pat. No. 5,045,317, which is incorporated herein by reference in its entirety for all purposes. The stem cell medium extract are any multipotent cell derived from human or plant stem cells used as a source of regenerative medicine. In one aspect of the invention, another active ingredient is Benzoyl Peroxide and all possible formulations of it.

In one aspect of the invention, the cannabinoid is hemp oil.

In a different aspect of the invention, the cannabinoid is one or more of cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), cannabidiorcol (CBD-$C_1$), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-$C_4$ (THCA-$C_4$), delta-9-tetrahydrocannabinol-$C_4$ (THC-$C_4$), delta-9-tetrahydrocannabivarinic acid (THCVA), delta-9-tetrahydrocannabivarin (THCV), delta-9-tetrahydrocannabiorcolic acid (THCA-$C_1$), delta-9-tetrahydrocannabiorcol (THC-$C_1$), delta-7-cis-iso-tetrahydrocannabivarin, delta-8-tetrahydrocannabinolic acid (.DELTA.$^8$-THCA), delta-8-tetrahydrocannabinol (.DELTA.$^8$-THC), cannabicyclolic acid (CBLA), cannabicyclol (CBL), cannabicyclovarin (CBLV), cannnabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-$C_4$ (CBN-$C_4$), cannabivarin (CBV), cannabinol-$C_2$ (CBN-$C_2$), cannabiorcol (CBN-$C_1$), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-metha-no-2H-1-benzoxocin-5-methanol (OH-iso-HHCV), cannabiripsol (CBR) and trihydroxy-delta-9-tetrahydrocannabinol (triOH-THC).

In yet another aspect of the invention, the cannabinoid is a cannabinoid receptor agonist. Preferably, the cannabinoid receptor agonist comprises one or more of a naphthoylindole, a naphthylmethylindole, a naphthoylpyrrole, a naphthylmethylindene, a phenylacetylindole, a cyclohexylphenol and a Palmitoylethanolamide (PEA).

In one embodiment of the invention, the benzoyl peroxide is present in the topical composition in a concentration between 0.1 and 10% by weight of the composition.

In one embodiment, the topical composition may further comprise a stabilizer. Preferably, the stabilizer is selected from the group consisting of guar gum, xanthan gum cellulose hyaluronic acid, polyvinyl pyrrolidone (PVP), alginate, chondritin sulfate, poly gamma glutamic acid, gelatin, chitisin, corn starch and flour, and is present in an amount from about 0.25% to about 30% (w/v).

In a preferred aspect of the invention, the topical composition is in the form of an ointment, a cream, an emulsion, a lotion, a paste, an unguent, a gel or a sunscreen. In yet another preferred aspect, the carrier in the topical composition comprises hemp oil.

In one embodiment, the topical composition further comprises one or more of a thickening agent, an antibiotic, an antiseptic agent, an antifungal, an antibacterial agent, an analgesic or an antiviral agent. In one aspect of the invention, the topical composition may further comprises a UV absorbing agent in an amount between 0.1 and 5% by weight of the composition.

In a different embodiment, the invention provides a method of treating skin, treating a skin disorder, or improving a condition of the skin in a subject in need thereof comprising topically administering to the subject the topical composition of the invention as described above. In one aspect of the invention, the skin disorder is one or more of atopic dermatitis or eczema, psoriasis, dermatitis, itching dermatosis, seborrheic dermatitis, rosacea, perioral dermatitis, acne, non-melanoma cancer or melanoma. In another aspect of the invention, the subject presents a symptom which is one or more of pruritus, dryness, skin rash, redness, swelling of the skin, itching, crusting, flaking, blistering, cracking, oozing, or bleeding. In yet another aspect, the dermatitis is atopic dermatitis, contact dermatitis, xerotic eczema, or seborrheic dermatitis. Preferably, the composition of the invention is topically administered to the subject in an amount between about 100 nmol to about 1 .mu.mol/cm$^2$. In one aspect of the invention, the subject is a mammal. In a preferred aspect of the invention, the mammal is a human.

In yet another embodiment, the invention provides a method for treating or preventing pruritus, dryness of the skin, skin rash, redness, swelling of the skin, itching, crusting, flaking, blistering, cracking, oozing, bleeding or blistering of the skin in a subject in need thereof, that comprises topically administering to the subject the composition of the invention. In one aspect of the invention, the subject has one or more of eczema, psoriasis, dermatitis, itching dermatosis, rosacea, perioral dermatitis, acne, non-melanoma cancer or melanoma. In one embodiment, the dermatitis is atopic dermatitis, contact dermatitis, xerotic eczema, or seborrheic dermatitis. Preferably, the composition of the invention is topically administered to the subject in an amount between about 100 nmol to about 1 .mu.mol/cm$^2$. In one aspect of the invention, the subject is a mammal. In a preferred aspect of the invention, the mammal is a human.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

FIG. 1 of US 2018/0021241A1, which is incorporated herein by reference in its entirety for all purposes, illustrates the chemical structure of some cannabinoids for use according to the invention.

DETAILED DESCRIPTION OF THE INVENTION

Cannabinoids are terpenophenolic compounds found in Cannabis sativa, an annual plant belonging to the Cannabaceae family. The plant contains more than 400 chemicals and approximately 80 cannabinoids. The latter accumulate mainly in the glandular trichomes. Natural phytocannabinoids occur in the free acid forms within plant tissue. For instance, the psychoactive cannabinoids tetrahydrocannbinol (THC), cannabidiol (CBD), cannabichromene (CBC) and cannabigerol (CBG) exist in their corresponding carboxylic acid forms THCA, CBDA, CBCA and CBGA within plant tissue and are converted to their active forms via non-enzymatic decarboxylation that occurs upon the drying of the plant tissue, or during storage or smoking.

The most active of the naturally occurring cannabinoids is tetrahydrocannabinol (THC), which is used for treating a wide range of medical conditions, including glaucoma, AIDS wasting, neuropathic pain, treatment of spasticity associated with multiple sclerosis, fibromyalgia and chemotherapy-induced nausea. Additionally, THC has been reported to be effective for the treatment of allergies, inflammation, infection, epilepsy, depression, migraine, bipolar disorders, anxiety disorder, drug dependency and drug withdrawal syndromes.

Cannabidiol (CBD), an isomer of THC, is a potent antioxidant and anti-inflammatory compound known to provide protection against acute and chronic neurodegeneration, and relief from chronic pain, inflammation, migraines, arthritis, spasms, epilepsy, and the like.

Cannabigerol (CBG), which is found in high concentrations in hemp, acts as a high affinity .alpha.$_2$-adrenergic receptor agonist, moderate affinity 5-HT$_1$A receptor antagonist and low affinity CB$_1$ receptor antagonist, and thus may have anti-depressant activity. Cannabichromene (CBC) possesses anti-inflammatory, anti-fungal and anti-viral properties. Tetrahydrocannabivarin (THCV) is known as an appetite suppressant.

The use of cannabinoids in topical compositions is limited by the fact that cannabinoids, because of their hydrophobic nature, must be dissolved in organic solvents that may irritate the skin.

Polyolprepolymers are polyalkylene glycol-based polyurethane polymers that readily deposit on and within the stratum corneum forming a reservoir rather than migrating further into the skin. In one aspect of the invention, the polyolprepolymers are present in the topical composition in a concentration between 0.1 and 30% by weight of the total composition. In other embodiments of the invention, the polyolprepolymers are present in the topical composition in a concentration between 0.1 and 25%, between 0.1 and 20%, between 0.1 and 15%, between 0.1 and 10%, or between 0.1 and 5% by weight of the total composition. This increases the efficacy of skin care formulations. This includes but is not limited to polyolprepolymer-2, polyolprepolymer-14 and polyolprepolymer-15, outlined in U.S. Pat. No. 5,045,317.

Alpha and beta hydroxy acids are chemical exfoliants. Alpha hydroxy acids are carboxylic acids characterized by the presence of one hydroxyl group attached to the .alpha.-position of the carboxyl group, known for their beneficial exfoliating properties and for inducing skin proliferation and new cell growth. Exemplary alpha-hydroxy acids include, but are not limited to, glycolic acid, lactic acid, malic acid, citric acid and tartaric acid. Alpha-hydroxy acids are different from beta-hydroxy acids, such as .beta.-hydroxybutanoic acid, which are carboxylic acids characterized by having one hydroxyl group attached to the .beta.-position of the carboxyl group.

In accordance with the present invention, it is contemplated herein that compositions containing polyolprepolymers, BV-OSC and stem cell extract in combination with one or more cannabinoids provide a number of advantages not found when either active agent is used by itself, including reduced skin irritation and fast healing of any skin condition that is enhanced by inflammation including, but not limited to, acne, aging spots, scar formation, eczema and wrinkles. Without being bound to any theory, it is believed that the cannabinoids of the inventive compositions modulate the cannabinoid receptors $CB_1R$ and $CB_2R$ located in the skin and involved in the attenuation of pain and contact allergic reaction, and thus stimulate the proliferation, growth and differentiation of keratinocytes in the skin as well as their immune competence and/or tolerance. Furthermore, it is believed that the combination of the cannabinoids with polyolprepolymers results in an unexpected synergic anti-inflammatory effect due to the anti-inflammatory properties of the cannabinoids, and contributes to the total wellness of the skin. Accordingly, the compositions containing a combination of one or more polyolprepolymers and one or more cannabinoids according to the invention provide greater skin improvement effects than the same compositions comprising either alone.

One embodiment of the invention is a topical composition for treating skin that comprises a therapeutically effective amount of at least one cannabinoid or molecule that acts on endocannabinoid receptors (e.g., Palmitoylethanolamide (PEA)), and a therapeutically effective amount of a polyolprepolymer, stem cell extract and BV-OSC (tetrahexyldecy ascorbate). In one embodiment of the invention, the stem cell extract is present in the topical composition in a concentration between 0.1 and 30% by weight of the composition. In other embodiments of the invention, the stem cell extract is present in the topical composition in a concentration between 0.1 and 25%, between 0.1 and 20%, between 0.1 and 15%, between 0.1 and 10%, or between 0.1 and 5%, by weight of the total composition. Likewise, in one aspect of the invention, the BV-OSC is present in the topical composition in a concentration between 0.1 and 30% by weight of the composition. In other embodiments of the invention, the BV-OSC is present in the topical composition in a concentration between 0.1 and 25%, between 0.1 and 20%, between 0.1 and 15%, between 0.1 and 10%, or between 0.1 and 5%, by weight of the total composition.

As used herein, the terms "cannabinoid" and "cannabinoids" include, but are not limited to, natural phytocannabinoids, organic cannabinoids, endocannabinoids, cannabinoid analogs, cannabinoid derivatives, synthetic cannabinoids and cannabinoid receptor agonists.

Examples of organic cannabinoids include, but are not limited to, hemp oil.

Examples of cannabinoids, cannabinoid analogs and cannabinoid derivatives include, but are not limited to, cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), cannabidiorcol (CBD-$C_1$), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-$C_4$ (THCA-$C_4$), delta-9-tetrahydrocannabinol-$C_4$ (THC-$C_4$), delta-9-tetrahydrocannabivarinic acid (THCVA), delta-9-tetrahydrocannabivarin (THCV), delta-9-tetrahydrocannabiorcolic acid (THCA-$C_1$), delta-9-tetrahydrocannabiorcol (THC-$C_1$), delta-7-cis-iso-tetrahydrocannabivarin, delta-8-tetrahydrocannabinolic acid (.$DELTA^8$-THCA), delta-8-tetrahydrocannabinol (.$DELTA^8$-THC), cannabicyclolic acid (CBLA), cannabicyclol (CBL), cannabicyclovarin (CBLV), cannnabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-$C_4$ (CBN-$C_4$), cannabivarin (CBV), cannabinol-$C_2$ (CBN-$C_2$), cannabiorcol (CBN-$C_1$), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CB TVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-metha-no-2H-1-benzoxocin-5-methanol (OH-iso-HHCV), cannabiripsol (CBR) and trihydroxy-delta-9-tetrahydrocannabinol (triOH-THC).

Cannabinoid receptor agonists as used herein may include natural and synthetic compounds that are structurally related to natural cannabinoids, and natural and synthetic compounds that are not structurally related to natural cannabinoids, all of which interact with at least one of the cannabinoid receptors. Cannabinoid receptor agonists that can be used according to the invention exert the same function as natural cannabinoids and share one or more common features with natural cannabinoids. For example, cannabinoid receptor agonists that are not structurally related to natural cannabinoids are lipid soluble and non-polar, consist of 22 to 26 carbon atoms and have a side-chain comprising more than four and up to nine saturated carbon atoms. Non-limiting examples of cannabinoid receptor agonists that are not structurally related to natural cannabinoids include naphthoylindoles, naphthylmethylindoles, naphthoylpyrroles, naphthylmethylindenes, phenylacetylindoles, such as benzoylindoles, cyclohexylphenols, and Palmitoylethanolamide (PEA).

Exemplary cannabinoid receptor agonists are well known in the art and include, but are not limited to, compounds of the molecular formula $C_{21}H_{30}O_2$; the molecular formula $C_{25}H_{38}O_3$; the molecular formula $C_{21}H_{34}O_2$; the molecular formula $C_{24}H_{23}NO$; the molecular formula $C_{22}H_{25}NO_2$; and the like.

Accordingly, the present invention provides a topical composition and methods for the treatment of a skin disorder or rejuvenation of the skin that comprise administering a topical composition, wherein the topical composition comprises a therapeutically effective amount of at least one cannabinoid and a therapeutically effective amount of at least one polyolprepolymers in a pharmaceutically acceptable carrier. Preferably, the carrier is an oil, cream or ointment.

In one aspect of the invention, the cannabinoids are present in the topical composition in a concentration between 0.1 and 30% by weight of the composition. In other embodiments of the invention, the cannabinoids are present in the topical composition in a concentration between 0.1 and 25%, between 0.1 and 20%, between 0.1 and 15%, between 0.1 and 10%, or between 0.1 and 5%, by weight of the total composition. Preferably, the cannabinoids are one or more of tetrahydrocannbinol (THC), cannabidiol (CBD), cannabigerol (CBG), cannabichromene (CBC), tetrahydrocannabivarin (THCV), analogs thereof, derivatives thereof, organic and synthetic cannabinoids and cannabinoid receptor agonists as described above. In one aspect of the invention, the cannabinoids in the topical composition comprise one or more of a natural phytocannabinoid, an organic cannabinoid, an endocannabinoid, a cannabinoid analog, a cannabinoid derivative, a synthetic cannabinoid and a cannabinoid receptor agonist. The cannabinoid receptor agonist may comprise one or more of a naphthoylindole, a naphthylmethylindole, a naphthoylpyrrole, a naphthylmethylindene, a phenylacetylindole, a cyclohexylphenol, and a Palmitoylethanolamide (PEA).

As used herein, the term "hydroxy acid" includes, but is not limited to, alpha-hydroxy acid and beta-hydroxy acid. The hydroxy acids are present in the topical composition in a concentration between 0.1 and 10% by weight of the composition. Alpha hydroxy acids that may be used according to the invention comprise, but are not limited to, organic carboxylic acids in which one hydroxyl group is attached to the alpha carbon of the acids. The generic structure of alpha hydroxy acids may be represented by the formula (Ra) (Rb) C (OH) COOH, wherein Ra and Rb are each H, F, Cl, Br, alkyl, aralkyl or aryl group of saturated or unsaturated, isomeric or non-isomeric, straight or branched chain or cyclic form, having 1 to 25 carbon atoms. Ra and Rb may also carry an OH, CHO, COOH or alkoxy group having 1 to 9 carbon atoms. The hydroxy acids may be present in the topical composition as a free acid or in lactone form, or in a salt form with an organic base or an inorganic alkali. The hydroxy adds may also exist as stereoisomers as D, L, and DL forms when Ra and Rb are not identical.

Typical alkyl, aralkyl and aryl groups for Ra and Rb include, but are not limited to, methyl, ethyl, propyl, isopropyl, butyl, pentyl, octyl, lauryl, stearyl, benzyl and phenyl. Alpha hydroxy acids include (1) alkyl alpha hydroxyacids; (2) aralkyl and aryl alpha hydroxyacids; (3) polyhydroxy alpha hydroxyacids; and (4) polycarboxylic alpha hydroxyacids.

Alkyl alpha hydroxy acids include, but are not limited to, 2-hydroxyethanoic acid (glycolic acid, hydroxyacetic acid) (H) (H) c (OH) COOH; 2-hydroxypropanoic acid (lactic acid) $(CH_3)$ (s) C (OH) COOH; 2-methyl 2-hydroxypropanoic acid (methyllactic acid) $(CH_3)$ $(CH_3)$ C (OH) COOH; 2-hydroxybutanoic acid $(C_2 H_5)$ (H) C (OH) COOH, 2-hydroxypentanoic acid $(C_3 H_7)$ (H) C (OH) COOH; 2-hydroxyhexanoic acid $(C_4 H_9)$ (H) C (OH) COOH; 2-hydroxyheptanoic acid $(C_5 H_{11})$ (H) C (OH) COOH; 2-hydroxyoctanoic acid $(C_6 H_{13})$ (H) C (OH) COOH; 2-hydroxynonanoic acid $(C_7 H_{15})$ (H) C (OH) COOH; 2-hydroxydecanoic acid $C_8 H_{17}$) (H) C (OH) COOH; 2-hydroxyundecanoic acid $(C_{10} H_{19})$ (H) C (OH) COOH; 2-hydroxydodecanoic acid (alpha hydroxylauric acid) $(C_{10} H_{21})$ (H) C (OH) COOH, 2-hydroxytetradecanoic acid (alpha hydroxymyristic acid) $(C_{12} H_{25})$ (H) C (OH) COOH; 2-hydroxyhexadecanoic acid (alpha hydroxypalmitic acid) $C_{14} H_{29}$) (H) C (OH) COOH; 2-hydroxyoctadecanoic acid (alpha hydroxystearic acid) $(C_{16} H_{14})$ (H) C (OH) COOH; 2-hydroxyeicosanoic acid (alpha hydroxyarachidonic acid) $(C_{18} H_{37})$ (H) (OH) COOH.

Aralkyl and aryl alpha hydroxy acids include, but are not limited to, 2-phenyl 2-hydroxyethanoic acid (mandelic acid) $(C_6 H_5)$ (H) C (OH) COOH; 2,2-diphenyl 2-hydroxyethanoic acid (benzylic acid) $(C_6 H_5)$ $(C_6 H_5)$ C (OH) COOH; 3-pphenyl 2-hydroxypropanoic acid (phenyllactic acid) $(C_6 H_5 CH_2)$ (H) C (OH) COOH; 2-pphenyl 2-methyl 2-hydroxyethanoic acid (atrolactic acid) $(C_6 H_5)$ $(CH_3)$ C (OH) COOH; 2-(4'-hydroxyphenyl)2-hydroxyethanoic acid (4-hydroxymandelic acid) (HO=$C_6 H_4$) (H) C (OH) COOH; 2-(4'-chlorophenyl) 2-hydroxyethanoic acid (4-chloromandelic acid) (Cl=$C_6 H_4$) (H) C (OH) COOH; 2-(3'-hydroxy-4'-methoxyphenyl) 2-hydroxyethanoic acid (3-hydroxy-4-methoxymandelic acid) (HO=, $CH_3$ O=$C_6 H_3$) (H) C (OH) COOH; 2-(4'-hydroxy-3'-methoxyphenyl) 2-hydroxyethanoic acid (4-hydroxy-3-methoxymandelic acid) (HO=, $CH_3$ O=$C_6 H_3$) (H) C (OH) COOH; 3-(2'-hydroxyphenyl) 2-hydroxypropanoic acid [3-(2'-hydroxyphenyl) lactic acid] HO=$C_6 H_4$=$CH_2$ (H) C (OH) COOH; 3-(4'-hydroxyphenyl) 2-hydroxypropanoic acid [3-(4'-hydroxyphenyl) lactic acid]HO=$C_6$=$CH_2$ (H) C (OH) COOH; and 2-(3',4'-dihydroxyphenyl) 2-hydroxyethanoic acid (3,4-dihydroxymandelic acid) HO=, HO=$C_6 H_3$ (H) C (OH) COOH.

Polyhydroxy alpha hydroxy acids include, but are not limited to, 2,3-dihydroxypropanoic acid (glyceiic acid) $(HOCH_2)$ (H) C (OH) COOH; 2,3,4-trihydroxybutanoic acid (isomers; erythronic acid, threonic acid) $HOCH_2$ (HO) $CH_2$ (H) C (OH) COOH; 2,3,4,5-tetrahydroxypentanoic acid (isomers; ribonic acid, arabinoic acid, xylonic acid, lyxonic acid) $HOCH_2$ (HO) $CH_2$(HO) $CH_2$ (H) C (OH) COOH; 2,3,4,5,6-pentahydroxyhexanoic acid (Isomers; allonic acid, altronic acid, gluconic acid, mannoic acid, gulonic acid, idonic acid, galactonic acid, talonic acid) $HOCH_2$ $(HO)CH_2$ $(HO)CH_2$ $(HO)CH_2$ (H) C (OH) COOH; and 2,3,4,5,6,7-hexahydroxyheptanoic acid (isomers; glucoheptonic acid, galactoheptonic acid etc.) $HOCH_2$ (HO) $CH_2$ (HO) $CH_2$ (HO) $CH_2$ (HO) $CH_2$ (H) C (OH) COOH.

Polycarboxylic alpha hydroxy acids include, but are not limited to, 2-hydroxypropane-1,3-dioic acid (tartronic acid) HOOC (H) C (OH) COOH; 2hydroxybutane-1,4-dioic acid (malic acid) HOOC $CH_2$ (H) C (OH) COOH; 2,3-dihydroxybutane-1,4-dioic acid (tartaric acid) HOOC (HO)CH (Hi) C (OH) COOH; 2-hydroxy-2-carboxypentane-1,5-dioic acid (citric acid) HOOC $CH_2$ C (OH) (COOH) $CH_2$ COOH; 2,3,4,5-tetrahydroxyhexane-1,6-dioic acid (isomers; saccharic acid, mucic acid etc.) HOOC $(CHOH)_4$ COOH.

Lactone forms include, but are not limited to, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

In a preferred aspect of the invention, the alpha hydroxy acid is lactic acid, citric acid, glycolic acid, mandelic acid, benzylic acid, malic acid, tartaric acid, gluconolactone, galactonolactone, glucuronolactone, galacturonolactone, gulonolactone, ribonolactone, saccharic acid lactone, pantoyllactone, glucoheptonolactone, mannonolactone, or galactoheptonolactone. In an additional preferred aspect of the invention, the beta-hydroxy acid is salicylic acid. In additional preferred aspects of the invention the polyolprepolymers is PP-2, PP-14, or PP-15. In additional preferred aspects of the invention, benzoyl peroxide is present from 0.1% up to 10% by weight of the total composition.

In one embodiment, the topical composition may further comprise a stabilizer. Preferably, the stabilizer is selected from the group consisting of guar gum, xanthan gum cellulose hyaluronic acid, polyvinyl pyrrolidone (PVP), alginate, chondritin sulfate, poly gamma glutamic acid, gelatin, chitisin, corn starch and flour, and is present in an amount from about 0.25% to about 30% (w/v).

In a preferred aspect of the invention, the topical composition is in the form of an ointment, a cream, an emulsion, a lotion, a paste, an unguent, a gel or a sunscreen. In yet another preferred aspect, the carrier in the topical composition comprises hemp oil.

Creams according to the inventions include water-in-oil or oil-in-water emulsions and may further comprise a cleansing agent, an emollient and an aromatic chemical compound.

Ointments and unguents according to the invention optionally contain oil and water in a ratio from 2:1 to 7:1, and may further comprise a wax, alcohols and petroleum-based mollifying agents.

Gels according to the invention optionally contain a vegetable oil up to 5% by weight of the total composition, water and a thickening agent. Preferably, the thickening agent is a natural polysaccharide, such as xanthan gum, carrageen, an alginate or cellulose gum.

Pastes according to the invention may optionally contain aloe gel and beeswax.

Lotions according to the invention include oil-in-water or water-in-oil emulsions and may comprise cetyl alcohol, an emulsifier, a fragrance, glycerol, petroleum jelly, a dye, one or more preservatives and a stabilizing agent.

A sunscreen composition according to the invention may further comprise a UV absorbing or barrier agent in an amount between 0.1 and 10% by weight of the composition. Exemplary UV-absorbing compounds include, but are not limited to, benzone compounds, glyceryl PABA, roxadimate, octocrylene, octyl methoxycinnamate, ethoxyethyl p-methoxycinnamate, homomenthyl salicylate, ethylhexyl salicylate, trolamine salicylate, ecamsule, ensulizole, bemotrizinol and bisoctrizole. Exemplary UV-barrier compounds include but are not limited to, zinc oxide and titanium dioxide.

In some embodiments, the topical compositions of the invention may further comprise one or more active agents, such as an antibiotic, an antiseptic agent, an antifungal, an antibacterial agent, an analgesic or an antiviral agent. In additional embodiments, the topical compositions of the invention may further comprise anesthetics, anti-cancer agents, antiacne agents, humectants, such as cationic, ionic and non-ionic surfactant, moisturizers, antipruritic agents, antiperspirants, antpsoriatic agents, antiseborrheic agents, antiaging and anti-wrinkle agents, skin lightening agents, depigmenting agents and vitamins.

Exemplary antibiotics include, but are not limited to, ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam. In one embodiment, the amount of the antibiotic in the composition is from 0.01 to 5% by weight of the total composition.

Antiseptic compounds include, but are not limited to, iodine, manuka honey, octenidine dihydrochloride, phenol, polyhexanide, sodium chloride, sodium hypochlorite, calcium hypochlorite, sodium bicarbonate, methyl paraben, benzoyl peroxide and sodium dehydroacetate. In one embodiment, the amount of the antiseptic compound in the topical formulation is from 0.01 to 5% by weight of the total composition.

Antifungal agents include, but are not limited to, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, and balsam of Peru. In one embodiment, the amount of the antifungal agent in the topical formulation is from 0.01 to 5% by weight of the total composition.

Analgesic agents include, but are not limited to, methyl salicylate, codeine, morphine, methadone, pethidine, buprenorphine, hydromorphine, levorphanol, oxycodone, fentanyl, and a non-steroidal anti-inflammatory drug. The amount of the analgesic agent in the topical formulation is from 0.01 to 5% by weight of the total composition.

Anti-viral agents include, but are not limited to, acyclovir, famciclovir, penciclovir, valacyclovir, trifluridine, docosanol, amantadine, rimantadine, oseltamivir, and zanamivir. The amount of the anti-viral agent in the topical formulation is from 0.01 to 5% by weight of the total composition.

In some embodiments, the topical composition of the invention may further comprise a stabilizer selected from the group consisting of guar gum, xanthan gum cellulose hyaluronic acid, polyvinyl pyrrolidone (PVP), alginate, chondritin sulfate, poly gamma glutamic acid, gelatin, chitisin, corn starch and flour, in an amount from about 0.25% to about 2% (w/v).

In some embodiments, the composition for topical application to the skin comprises a therapeutically effective amount of at least one cannabinoid, a therapeutically effective amount of polyolprepolymers.

The cannabinoids according to the invention may be obtained as an extract from a cannabis plant for medical use, such as Cannabis sativa and Cannabis indica, by extracting the trichomes of the plants in a solvent and heating the mixture to evaporate the solvent. Examples of extraction technologies that may be used include, but are not limited to, $CO_2$ extraction and microwave extraction. The cannabinoids according to the invention may also be obtained as an extract from a cannabis transgenic plant that overexpresses one or more particular cannabinoids or that does not express or under-expresses one or more particular cannabinoids. Synthetic cannabinoids may be prepared according to the technologies known to those skilled in the art. In the alternative, endogenous nucleic acid sequences may be extracted from a cannabis plant and used to produce cannabinoids by recombinant technology.

The topical compositions of the invention may be prepared by dissolving the dry extracts of cannabinoids in an oil, and by adding the cannabinoid solution to a composition containing the hydroxy acids. The hydroxy acid composition may be an alcohol solution in which the hydroxy acids are dissolved, or the hydroxy acids may be dissolved in an alcohol-free solution. In an alternative embodiment, the hydroxy acids are dissolved in a composition comprising hemp oil or one or more cannabinoid, analogs thereof, derivatives thereof, organic and synthetic cannabinoids and cannabinoid receptor agonists as described above, wherein the one or more cannabinoids, analogs thereof, derivatives thereof, organic and synthetic cannabinoids and cannabinoid receptor agonists are dissolved in an oil. Preferably, the oil is a vegetable oil. Even more preferably the vegetable oil is hemp oil.

In a different embodiment, the invention provides a method to treat a skin disorder or rejuvenate the skin in a subject in need thereof, that comprises topically administering to the subject the topical composition of the invention as described above. The skin disorder may be one or more of eczema, psoriasis, dermatitis, itching dermatosis, rosacea, perioral dermatitis, acne, non-melanoma cancer or melanoma. The subject may present the first signs of irritation, or presents a severe symptom which is one or more of pruritus, dryness, skin rash, redness, swelling of the skin, itching, crusting, flaking, blistering, cracking, oozing, and bleeding. The dermatitis may be atopic dermatitis, contact dermatitis, xerotic eczema, or seborrheic dermatitis. In a preferred embodiment, the composition of the invention is topically administered to the subject in an amount between about 100 nmol to about 1 .mu.mol/cm$^2$. In one aspect of the invention, the subject is a mammal. In a preferred aspect of the invention, the mammal is a human.

In yet another embodiment, the invention provides a method for treating or preventing pruritus, dryness of the skin, skin rash, redness, swelling of the skin, itching, crusting, flaking, blistering, cracking, oozing, bleeding or blistering of the skin in a subject in need thereof, that comprises topically administering to the subject the composition of the invention. The subject may be disease-free or may be suspected of having or have one or more skin conditions, such as eczema, psoriasis, dermatitis, itching dermatosis, rosacea, perioral dermatitis, acne, non-melanoma cancer or melanoma. The dermatitis may be atopic dermatitis, contact dermatitis, xerotic eczema, or seborrheic dermatitis. In a preferred embodiment, the composition of the invention is topically administered to the subject in an amount between about 100 nmol to about 1 .mu.mol/cm$^2$. In one aspect of the invention, the subject is a mammal. In a preferred aspect of the invention, the mammal is a human.

The present invention thus generally described, will be understood more readily by reference to the following examples, which are provided by way of illustration only, and are not intended to be limiting the present invention.

EXAMPLES

Example 1

Treatment of Dermatitis 30 subjects with severe dermatitis are divided into two groups, 5 subjects per group. The subjects are instructed to topically apply a cream two times daily for two weeks. Group one is treated for two weeks with a cream containing hydroxyl acids, polyolprepolymer, stem cell extract and vehicle. Group two is treated for two weeks with a cream containing the hydroxyl acids, polyolprepolymer, stem cell extract, vehicle and cannabinoids. The effects of the different treatments are evaluated after two weeks.

The invention claimed is:

1. A topical emulsion consisting essentially of an isolated cannabinoid selected from the group consisting of cannabigerolic acid, cannabigerolic acid monomethylether, cannabigerol, cannabigerol monomethylether, cannabigerovarinic acid, cannabigerovarin, cannabichromenic acid, cannabichromene, cannabichromevarinic acid, cannabichromevarin, cannabidiolic acid, cannabidiol, cannabidiol monomethylether, cannabidiol-C4, cannabidivarinic acid, cannabidivarin, cannabidiorcol and mixtures thereof; a stem cell extract; and a polyolprepolymer.

2. The topical emulsion of claim 1, wherein the cannabinoid is present in a concentration between 0.1 and 30% by weight of the topical emulsion; and wherein the polyolprepolymer is present in a concentration between 0.1 and 10% by weight of the topical emulsion.

3. The topical emulsion of claim 1, wherein the polyolprepolymer is polyolprepolymer-2, -14, or -15, or a combination thereof.

4. The topical emulsion of claim 1, further consisting essentially of tetrahexylecyl ascorbate.

5. The topical emulsion of claim 1, further consisting essentially of a component selected from the group consisting of an alpha hydroxy acid, a lactic acid, citric acid, glycolic acid, mandelic acid, benzylic acid, malic acid, tartaric acid, gluconolactone, galactonolactone, glucuronolactone, galacturonolactone, gulonolactone, ribonolactone, saccharic acid lactone, pantoyllactone, glucoheptonolactone, mannonolactone, galactoheptonolactone and mixtures thereof.

6. The topical emulsion of claim 1, further consisting essentially of a benzoyl peroxide.

7. The topical emulsion of claim 1, further consisting essentially of a hydroxy acid.

8. The topical emulsion of claim 1, further consisting essentially of a stabilizer selected from the group consisting of guar gum, xanthan gum, cellulose, hyaluronic acid, polyvinyl pyrrolidone, alginate, chondritin sulfate, poly gamma glutamic acid, gelatin, chitosin, corn starch, flour and mixtures thereof, in an amount from about 0.25% to about 30% (w/v).

9. The topical emulsion of claim 1, further consisting essentially of hemp oil.

10. The topical emulsion of claim 1, further consisting essentially of one or more of a thickening agent, an antibiotic, an antiseptic agent, an antifungal, an analgesic, an antiviral agent or a UV absorbing agent in an amount between 0.1 and 5% by weight of the composition;

wherein the thickening agent is selected from the group consisting of xanthan gum, carrageen, an alginate and cellulose gum;

wherein the antibiotic is selected from the group consisting of ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, and mixtures thereof;

wherein the antiseptic agent is selected from the group consisting of iodine, manuka honey, octenidine dihydrochloride, phenol, polyhexanide, sodium chloride, sodium hypochlorite, calcium hypochlorite, sodium bicarbonate, methyl paraben, benzoyl peroxide, sodium dehydroacetate, and mixtures thereof;

wherein the antifungal is selected from the group consisting of amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam, and mixtures thereof;

wherein the analgesic is selected from the group consisting of methyl salicylate, codeine, morphine, methadone, pethidine, buprenorphine, hydromorphine, levorphanol, oxycodone, fentanyl, and mixtures thereof;

wherein the antiviral agent is selected from the group consisting of acyclovir, famciclovir, penciclovir, valacyclovir, trifluridine, docosanol, amantadine, rimantadine, oseltamivir, zanamivir, and mixtures thereof; and wherein the UV absorbing or barrier agent is selected from the group consisting of benzone compounds, glyceryl PABA, roxadimate, octocrylene, octyl methoxycinnamate, ethoxyethyl p-methoxycinnamate, homomenthyl salicylate, ethylhexyl salicylate, trolamine salicylate, ecamsule, ensulizole, bemotrizinol, bisoctrizole, zinc oxide, titanium dioxide, and mixtures thereof.

11. A method to treat a skin disorder or rejuvenate the skin in a human in need thereof consisting essentially of topically administering to the human the topical emulsion of claim 1.

12. The method of claim 11, wherein the skin disorder is selected from the group consisting of eczema, psoriasis, dermatitis, itching dermatosis, rosacea, perioral dermatitis, acne, and melanoma.

13. The method of claim 11, wherein the condition of the human's skin is selected from the group consisting of pruritus, dryness, skin rash, redness, swelling of the skin, itching, crusting, flaking, blistering, cracking, oozing, and bleeding.

14. The method of claim 12, wherein the dermatitis is selected from the group consisting of atopic dermatitis, contact dermatitis, xerotic eczema, and seborrheic dermatitis.

15. The method of claim 11, wherein the topical emulsion is administered to the human in an amount between about 100 nmol to about 1 micro mol/cm2.

* * * * *